(12) United States Patent
Kalachev et al.

(10) Patent No.: US 7,309,864 B2
(45) Date of Patent: Dec. 18, 2007

(54) METHOD FOR ANALYSING PHYSICAL AND/OR CHEMICAL PROPERTIES OF THE SURFACE LAYER OF A SOLID BODY (VARIANTS)

(75) Inventors: Alexei Alexandrovich Kalachev, Berlin (DE); Nikolai Mikhailovich Blashenkov, Sankt-Peterburg (RU); Yury Petrovich Ivanov, Sankt-Peterburg (RU); Vladimir Antonovich Kovalsky, Sankt Peterburg (RU); Alexandr Lyovich Myasnikov, Sankt-Peterburg (RU)

(73) Assignee: Alexey Alexandrovich Kalachev, Berlin (DE)

( * ) Notice: Subject to any disclaimer, the term of this patent is extended or adjusted under 35 U.S.C. 154(b) by 0 days.

(21) Appl. No.: 10/527,966

(22) PCT Filed: Jul. 15, 2003

(86) PCT No.: PCT/RU03/00311

§ 371 (c)(1),
(2), (4) Date: Oct. 20, 2005

(87) PCT Pub. No.: WO2004/025275

PCT Pub. Date: Mar. 25, 2004

(65) Prior Publication Data

US 2006/0145067 A1 Jul. 6, 2006

(30) Foreign Application Priority Data

Sep. 16, 2002 (RU) ............................. 2002125410

(51) Int. Cl.
*G01N 25/02* (2006.01)
(52) U.S. Cl. .................. 250/310; 374/17; 374/161

(58) Field of Classification Search ................ 374/17, 374/161
See application file for complete search history.

(56) References Cited

U.S. PATENT DOCUMENTS 5,683,179 A * 11/1997 Lowry ........................ 374/17

FOREIGN PATENT DOCUMENTS

| SU | 928204 A | 5/1982 |
| SU | 1783405 A1 | 12/1992 |

OTHER PUBLICATIONS

V.A.Bershtein, V.M.Egorov, "Differential Scanning Calorimetry in Physics and Chemistry of Polymers", "Khimiya", Leningrad, 1990, pp. 74-81.
Ya. Rabek, "Experimental Methods in Polymer Chemistry", v.1, Moscow, "Mir", 1983, p. 337.
A.Gzanderna "Methods of Surface Analysis", Moscow, "Mir", 1979, pp. 63-64, 76-77, 83-84, 88-89.
.A.Kalachev, etc., Plasma-induced Thermoluminescence—a New Method for Investigating Supramolecular Architectures and Temperature Transitions in Polymers and Other Solid Sur.
JP 2002148157 A (Mitsubishi Chemicals Corp) May 22, 2002.

* cited by examiner

*Primary Examiner*—David A. Vanore
(74) *Attorney, Agent, or Firm*—John D. Gugliotta (57) ABSTRACT

According to the method for analyzing physical and/or chemical properties of the surface layer of a solid as per claim 1, the surface layer is activated by a unit irradiation pulse and, when the irradiation is over, is deactivated by keeping the solid at a constant temperature and subsequently heating it, the spectrum of the energy quanta emitted by the surface layer of the solid is recorded during the deactivation; the spectrum of the emitted energy quanta recorded at a constant temperature provides data on the loosely coupled states of the surface layer and their half-lives and the thermoluminescence spectrum recorded during the heating gives information on phase and relaxation transition temperatures in the surface layer.

1 Claim, 13 Drawing Sheets

METHOD FOR ANALYSING PHYSICAL AND/OR CHEMICAL PROPERTIES OF THE SURFACE LAYER OF A SOLID BODY (VARIANTS)

FIELD OF THE INVENTION

The invention relates to analysis of structures of surface and near-surface layers of solids and their physical and chemical properties using activating actions.

BACKGROUND OF THE INVENTION

Since the structure of a surface layer of a solid differs substantially from the structure of the solid in the bulk and in many respects governs its behavior in different media and in the fields of various forces, the information on the surface layer of a solid opens up the way to the scientifically-based modification of the surfaces of solids with the purpose of obtaining materials with desirable optical, mechanical, adhesive, electrical, luminescent and other properties, as well as to the control of many processes important in the practical respect, such as crystal growth, epitaxial and plasma chemical growth of layers, catalysis, preparation of ultrathin film structures by the Langmuir-Blodgett and molecular self-assembly techniques, strengthening of materials, etc. It also allows one to control the surface quality (surface defectoscopy) of industrial products with a higher precision, which is especially important in such fields as protective coatings and micro/nano electronics.

Methods for analyzing physical properties of solids, in particular temperatures and activation energies of phase and relaxation transitions in materials, by means of differential scanning calorimetry (see V. A. Bershtein, V. M. Egorov, "Differential Scanning Calorimetry in Physics and Chemistry of Polymers", "Khimiya", Leningrad, 1990, pp. 74-81) and by means of nuclear magnetic resonance (see Ya. Rabek, "Experimental Methods in Polymer Chemistry", v. 1, Moscow, "Mir", 1983, p. 337) are known.

A disadvantage of these methods is that they mainly characterize the properties of the sample bulk and do not give proper information on the sample surface layer.

A technique for analyzing physical properties of the surface layer of a solid, in particular determination of temperatures and activation energies of phase and relaxation transitions, involving surface bombardment with primary beams of neutral atoms and/or electrons and/or ions and/or photons and/or X-rays and detection of secondary beams of the corresponding charged particles (see, for example, A. Gzanderna "Methods of Surface Analysis", Moscow, "Mir", 1979, pp. 63-64, 76-77, 83-84, 88-89 (a copy of the pages referred to is attached)) is known.

This technique is taken as a prototype of the variant of the method as per claim 1 of the present invention.

When the surface layer of a solid is probed (bombarded), charged particles (electrons, ions), neutral particles (atoms, molecules), and photons are emitted. The surface layer is investigated under constant bombardment, the quantity, energy and spatial distribution (angles of departure) of the emitted particles being detected. However, said method that involves continuous bombardment of the surface gives rise to undesirable modifications of the surface layer investigated. Moreover, since the experiment is typically carried out at a constant temperature of a solid, this method cannot give information on temperatures and energies of phase and relaxation transitions in the surface layer; if the experiments are performed on one and the same sample at several temperatures, the sample surface undergoes multiple bombardments, which results in even more severe changes of the sample surface and, hence, in unreliable transition parameters.

A method for analyzing physical properties of the surface layer of a solid is known, involving the activation of the surface layer of a solid by low-temperature plasma (LTP) followed by deactivation of the surface layer during which a thermoluminescence spectrum is recorded. The LTP used in this method is ignited by an unmodulated voltage with a frequency of 40.68 MHz at a 10-Pa pressure of a plasma-generating gas, the duration of the sample activation by LTP being from 10 s to 9 min (see A. A. Kalachev, etc., "Plasma-induced Thermoluminescence—a New Method for Investigating Supramolecular Architectures and Temperature Transitions in Polymers and Other Solid Surfaces", Applied Surface Science 70/71 (1993), pp. 295-298 (a copy is attached)).

This engineering solution is taken as a prototype of the variant of the method as per claim 3 of the present invention.

The disadvantage of the prototype method is a modifying influence of the LTP with said parameters upon the surface layer of the sample investigated, which results in insufficiently reliable information on physical and chemical properties of this layer. First of all, this is due to strict plasma parameters used in the prototype, namely, a high pressure of a plasma-generating gas (10 Pa) and relatively long (10 s and more) duration of plasma activation. Both factors lead to overheating of the surface layer and a decay of arising active states already in the course of plasma treatment. For example, as seen from FIG. 4 of the prototype, the luminescence intensity typically falls with increasing treatment time. Moreover, said strict plasma parameters lead to other physical-chemical changes in the surface layer being analyzed.

In addition, in the mode of isothermal luminescence (see FIG. 3, paper by A. A. Kalachev etc.) the curves obtained according to the known method and illustrating the dependence (decrease) of thermoluminescence on time from the moment the LTP activation of the sample is over have no characteristic features; therefore, during this period of time no useful information on the surface structure or surface physical-chemical processes was obtained using said method. The curves are only used as a means for the determination of the moment when heating aimed at deactivation of the surface layer of a solid has to be started.

SUMMARY OF THE INVENTION

The object of the present invention is to decrease the modifying influence of activating irradiation upon the surface layer of a solid and to increase the informativity and accuracy of measurements.

According to the invention as per the first variant (claim 1), the method for analyzing physical and/or chemical properties of the surface layer of a solid comprises the activation of the surface layer of a sample by irradiation in the form of an atom beam and/or electron beam and/or molecular beam and/or ion beam and/or photon beam and/or their combination, deactivation of the surface layer, and recording of the spectrum of the energy quanta emitted by the surface layer; the surface layer is subjected to a unit irradiation pulse and, when the irradiation is over, is deactivated by keeping the solid at a constant temperature and subsequently heating it; the spectrum of the energy quanta emitted by the surface layer of the solid is recorded during the deactivation; the spectrum of the emitted energy quanta recorded at a constant temperature provides data on loosely coupled states of the surface layer and their half-lives and the thermoluminescence spectrum recorded during the heating gives information on the phase and relaxation transition temperatures in the surface layer; as per the second variant (claim 2), the irradiation pulse activating the surface has a power from $10^{-5}$ to $10^{-3}$ W/cm$^2$.

An important property of the method resulting from implementation of the distinguishing features of the first variant of the method is that it gives possibility to analyze the radiation spectra after the end of the bombardment of the surface of a sample with atoms, electron, ions etc. rather than during the bombardment of the surface by the particles. Due to the activation of the surface layer of a solid by a unit irradiation pulse of low power, subsequent deactivation of the surface layer, and detection of emitted energy (light energy) quanta after the end of the bombardment of the surface layer, the irradiation modifying influence becomes considerably weaker, and the accuracy and reliability of measurements increases.

According to the invention as per the second variant (claim 3), the method for analyzing physical and/or chemical properties of the surface layer of a solid comprising activation of said surface layer by low-temperature plasma followed by deactivation of the surface layer and recording of the thermoluminescence spectrum uses the low-temperature plasma with a plasma-forming gas pressure from 4 to 8 Pa for a period of time from 0.05 s to 5 s; radiation spectra are recorded at a constant temperature of the sample; additional information on physical and chemical reactions in the surface layer of the solid is obtained from the curves showing the decrease in isothermal luminescence from the moment of termination of the sample activation by the low-temperature plasma. It is preferable to use the plasma with a power from $10^{-5}$ to $10^{-3}$ W/cm$^3$ in the second variant of the method.

Along with an unmodulated high-frequency field ($10^6$-$10^{12}$ Hz) igniting the plasma, DC discharges, low-frequency discharges (1-$10^5$ Hz), and high-frequency discharges modulated by a low frequency can be used in the method of the present invention. Pulsed discharges with duration of a pulse and interval between pulses in the range $10^{-6}$-$10^2$ s can also be used. Moreover, the method of the present invention provides for an opportunity to vary the potential between the sample holder and the plasma.

The different types of the plasma used lead to different densities of arising luminescent surface centers, to variations of the types of these centers and their distribution across the thickness of the surface layer, i.e., the use of the abovementioned different types of discharges and any combination of these discharges widen the technological opportunities and expand the range of analyzed objects.

The implementation of the distinguishing features of the second variant of the method leads to a considerable reduction in the modifying influence of LTP upon the surface layer of a solid. Furthermore, when a suggested reduction in the pressure of the plasma-generating gas and a decrease in the LTP activation time of the surface layer of the sample were accomplished, a new quite paradoxical effect was discovered. This effect consists in the fact that in the mode of isothermal luminescence the curves characterizing the decay of the luminescence intensity with time after the end of the LTP activation exhibit characteristic features that give information on physical and chemical reactions in the surface layer of the solid, which could not be obtained with the LTP parameters used in the prototype.

The applicant has not found any sources of information containing data on the engineering solutions identical to the claimed ones. In the applicant's opinion, this suggests that the invention conforms to the criterion "novelty" (N).

The applicant has not found any data on the influence of the distinguishing features of the invention on the achievable technical result. This suggests that the claimed engineering solution conforms to the criterion "inventive step" (IS).

BRIEF DESCRIPTION OF THE DRAWINGS

Hereinafter the invention is illustrated by a detailed description of its embodiment with references to drawings as follows.

PREFERRED EMBODIMENT

Figure 1:
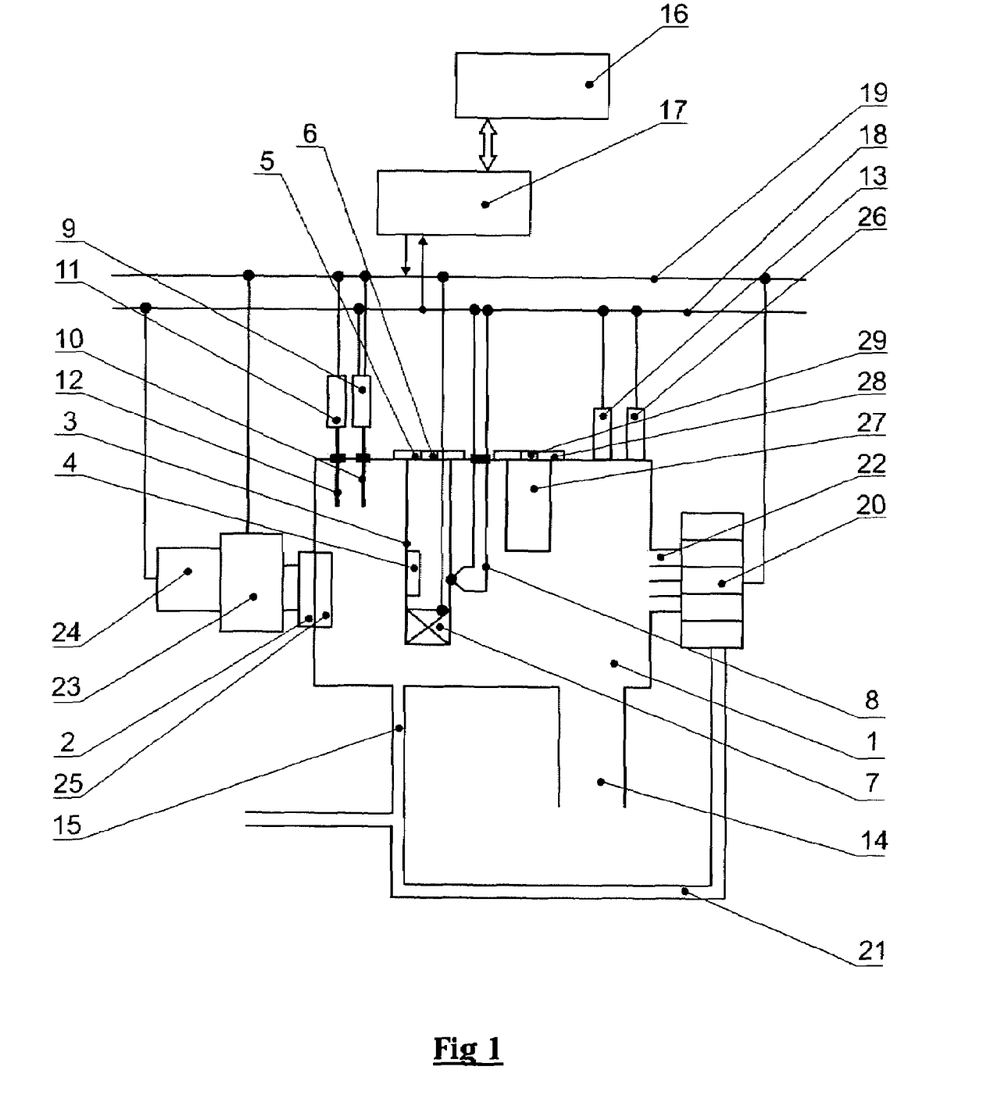
FIG. 1 is a schematic diagram of the device used to implement the method of the present invention.

The device for the implementation of the method in the particular embodiment comprises a vacuum chamber 1 made of stainless steel and equipped with an optical window 2 made of optical quartz. The vacuum chamber 1 contains a sample holder in the form of a copper container 3. A sample 4 of a solid to be investigated is attached to its outer surface. In the given embodiment the sample 4 is fixed with the help of springs (not shown in the drawing). The container 3 is covered with a lid 5 having an orifice 6 for feeding a coolant, in particular liquid nitrogen. A heater 7 is located in the container 3, and a chromel-alumel thermocouple 8 is placed on its outer surface. The device also contains a generator 9 that produces electromagnetic oscillations with a frequency of 16 MHz. An electrode 10 of the generator 9 is inserted into the vacuum chamber 1. An initiator 11 of electric discharge is a high-voltage transformer; on closing-breaking the circuit of the primary winding, it delivers 20-kV pulses from the secondary winding which are applied to an electrode 12 located in the vacuum chamber 1. The electric discharge duration is set by a timer (not shown in the drawing). A "barotron"-type gauge 13 of low vacuum is located on the outer surface of the vacuum chamber 1 and communicates with it. The vacuum chamber 1 is equipped with a main 14 for producing vacuum of down to $1.33 \cdot 10^{-5}$ Pa in it and also with a main 15 for delivering gases into the vacuum chamber. Hydrogen is used in the given embodiment, but other gases, such as oxygen, nitrogen, inert gases, etc., can also be used. The device contains a system for treatment of the obtained information that comprises a computer 16 with a monitor and an interface 17 between the computer 16 and a data acquisition bus 18. The interface 17 comprises an AD-7858 analog-digital converter, an AD8080 microprocessor and a source of voltages for different blocks of the device which are supplied to a bus 19. Commands are issued from the computer 16 through the interface 17 to the bus 19.

The device comprises a unit 20 for generating an atom and/or molecular and/or ion and/or electron and/or photon beam. In the given embodiment the unit 20 comprises an atomizer with an element in the form of an aggregate of capillaries 20 μm in diameter for formation of a narrow beam, a system for generating a molecular beam comprising a main 21 for delivering gas and an element in the form of an aggregate of capillaries of the same diameter, an ion gun, an electron gun, and a DRSH-100 mercury lamp for generating a photon beam. The unit 20 also comprises a facility for forming pulses of the above mentioned beams including valves, blocking electrodes, etc. An output 22 of the unit 20 is coupled to the vacuum chamber 1. A facility for analysis of the wavelengths of the light emitted by the surface of the sample 4 is located between the facility for detection of the emitted light and the sample. In the given embodiment, the facility for analysis comprises an MDR-3 monochromator 23 with a PHEU-68 photomultiplier 24 connected to its output (light filters can be used instead of the monochromator in particular cases). The monochromator 23 placed in front of the outer side of the optical window 2 which is shielded by a screen 25 placed inside the vacuum chamber 1 to cut off the radiation that could cause luminescence of the material of the window 2 or malfunction of the detector in the course of sample activation (for example, "PHEU blinding"). Moreover, the device has a PMI-2 gauge 26 of high vacuum attached to the outer surface of the vacuum chamber 1 and communicating with it. The device also contains a trap 27 for a coolant equipped with a lid 28 having an orifice 29 for filling the trap with a coolant. The trap 27 is placed in the vacuum chamber 1.

The method as per claim 1 is implemented as follows.

The sample 4 is fixed to the sample holder in the form of the container 3 and placed into the vacuum chamber 1; the air is evacuated from the vacuum chamber 1 through the main 14 down to a pressure of $1.33 \cdot 10^{-5}$ Pa. The pressure is controlled by the high-vacuum gauge 26. Then the trap 27 is filled with the coolant, which results in adsorption of residual gases and water vapors on its surface. The optical window 2 is cut off from the radiation of the vacuum chamber by the screen 25. Then necessary commands are issued from the computer 16 through the interface 17 and the bus 19 to the unit 20 for generating an atom and/or molecular and/or ion and/or electron and/or photon beam, and the sample surface is subjected to the action of a pulse of any beam mentioned above or to successive actions of the pulses of different beams. In order to generate atom and molecular beams, a gas (hydrogen in the particular embodiment) is fed into the beam-generating unit 20 through the main 21. The total irradiation power per unit area of the investigated surface lies within the range $10^{-5}$-$10^{-3}$ W/cm$^2$. After the irradiation, the solid is kept at a constant temperature, and a spectrum of the energy quanta, in particular light, emitted by the surface layer of the solid is recorded. In order to analyze the light wavelengths and detect their intensity, the monochromator 23 and the photomultiplier 24 are used; the output signal from the photomultiplier 24 comes to the data collection bus 18 and further, through the interface 17, to the computer 16. Then in the particular embodiment the sample 4 is heated by the heater 7, the sample temperature being controlled by the thermocouple 8 (in particular cases other means of temperature control can be used). Signals from the thermocouple 8 and the photomultiplier 24 come to the data acquisition bus 18 and, through the interface 17, to the computer 16 for further processing.

Figure 2:
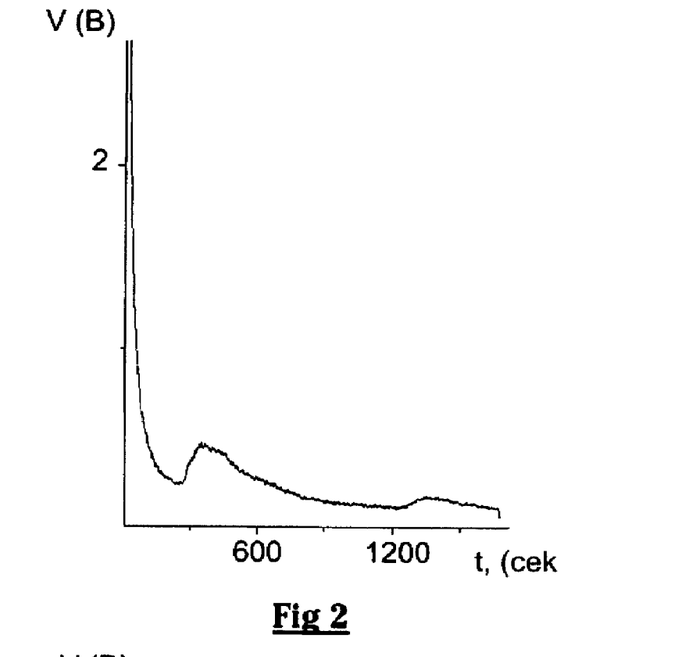
FIG. 2 shows a constant-temperature spectrum of the light emitted by a sample surface activated by an atom beam (example 1)
Figure 3:
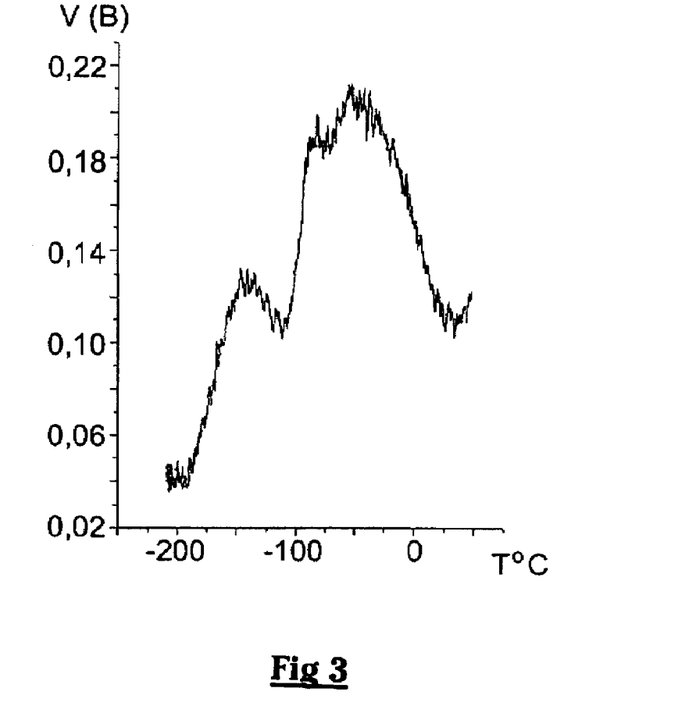
FIG. 3 shows a spectrum of the light emitted by a sample surface activated by an atom beam and then heated (example 1)

In example 1, the surface layer of low-pressure polyethylene MOPLEN ($M_w$=114000) crystallized at the temperature close to the melting temperature was subjected to irradiation in the form of a unit pulse of a hydrogen atom beam. The irradiation power per unit area of the investigated surface was $2 \cdot 10^{-5}$ W/cm$^2$. The recorded spectrum of the energy quanta emitted by the surface of the polyethylene sample at a constant temperature is presented by a graph in FIG. 2. The graph exhibits two maxima that provide information on loosely coupled states of the surface layer of the material and half-lives of these states. When the material was heated, a thermoluminescence spectrum was recorded (FIG. 3). The positions of maxima in the thermoluminescence spectrum give information on the phase and relaxation transition temperatures in the surface layer of the sample investigated.

Figure 4:
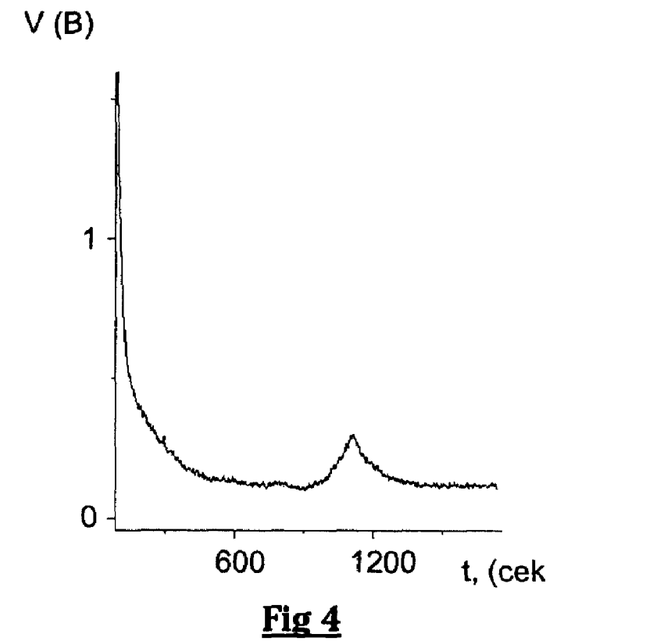
FIG. 4 shows a constant-temperature spectrum of the light emitted by a sample surface activated by an atom beam (example 2)
Figure 5:
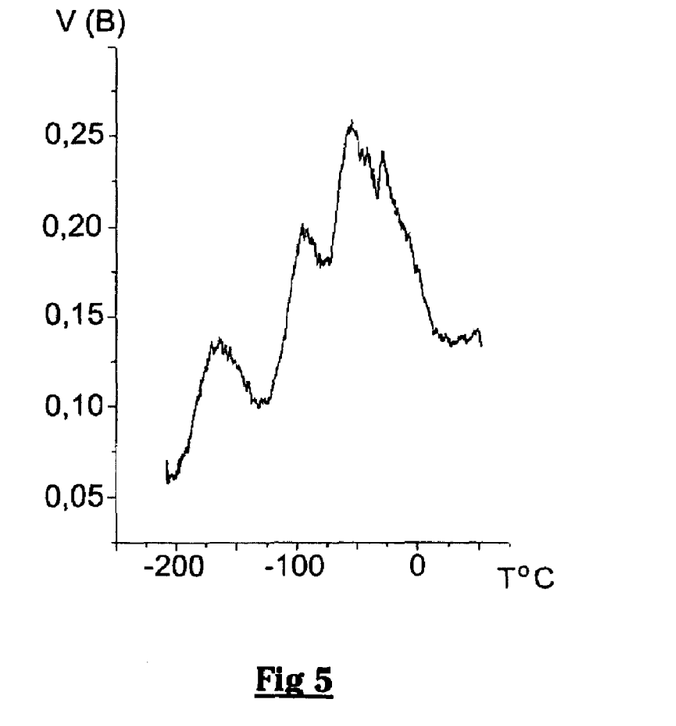
FIG. 5 shows a spectrum of the light emitted by a sample surface activated by an atom beam and then heated (example 2)
Figure 6:
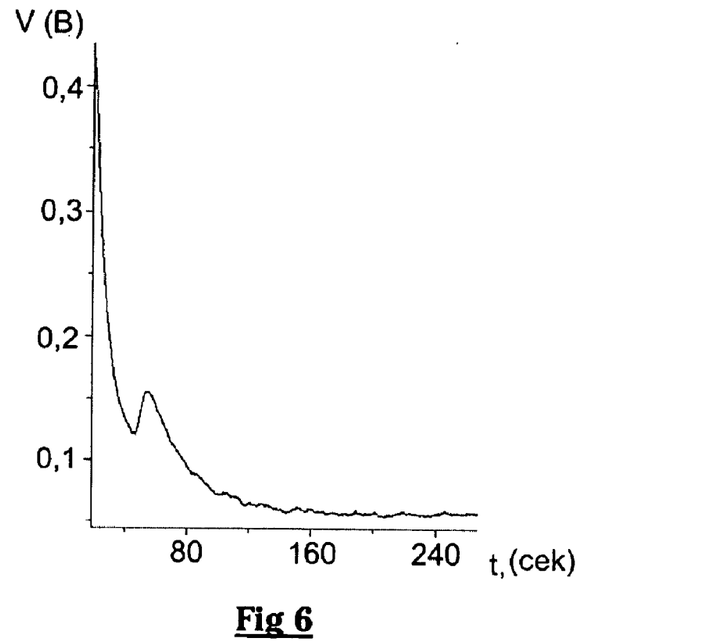
FIG. 6 shows a constant-temperature spectrum of the light emitted by a sample surface activated by an atom beam (example 3)
Figure 7:
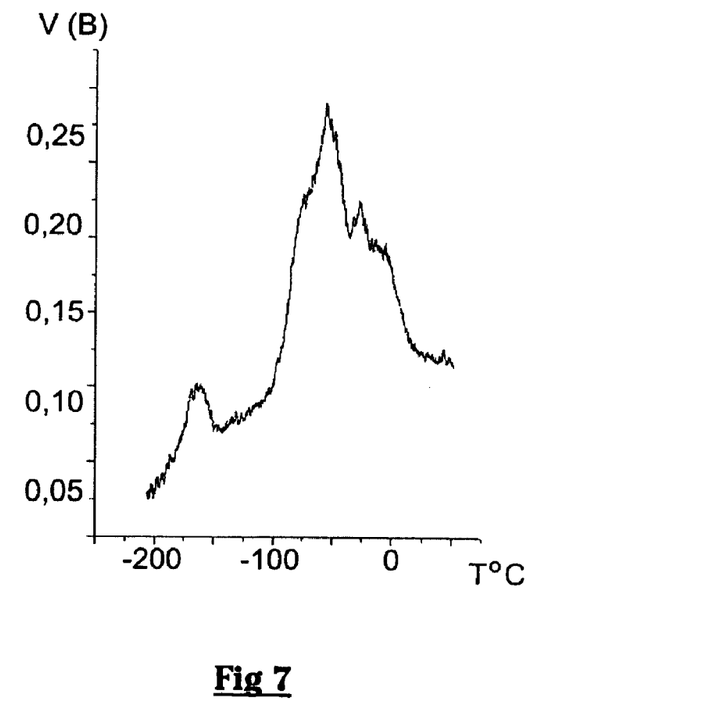
FIG. 7 shows a spectrum of the light emitted by a sample surface activated by an atom beam and then heated (example 3)
Figure 8:
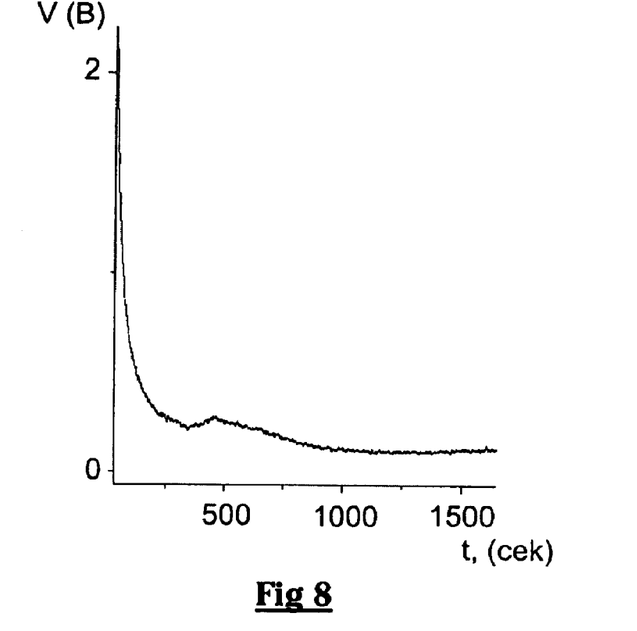
FIG. 8 shows a constant-temperature spectrum of the light emitted by a sample surface activated by a molecular beam (example 3)
Figure 9:
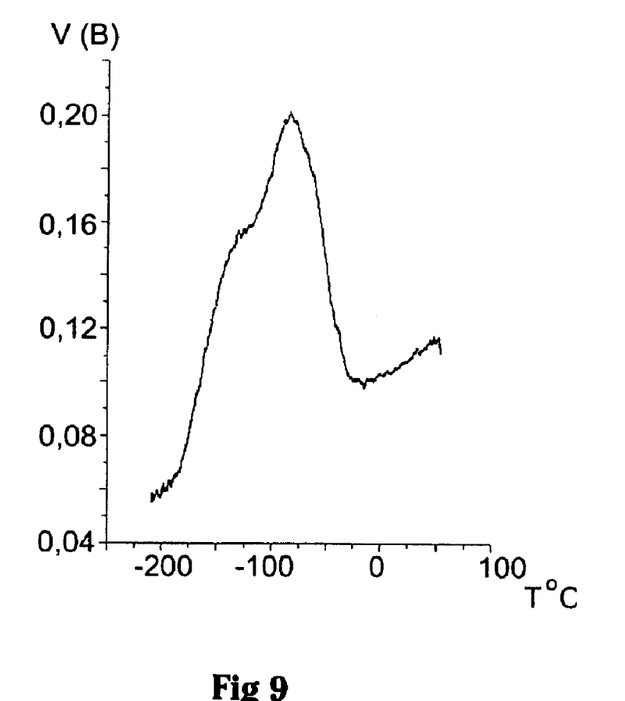
FIG. 9 shows a spectrum of the light emitted by a sample surface activated by a molecular beam and then heated (example 3)
Figure 10:
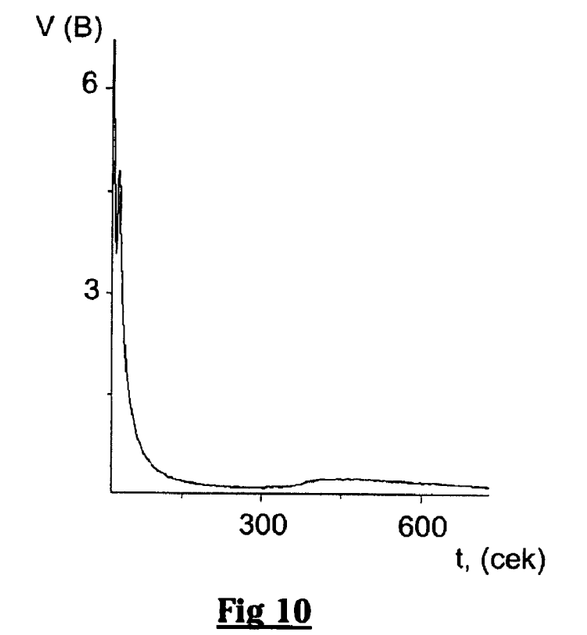
FIG. 10 shows a constant-temperature spectrum of the light emitted by a sample surface activated by an ion beam (example 3)
Figure 11:
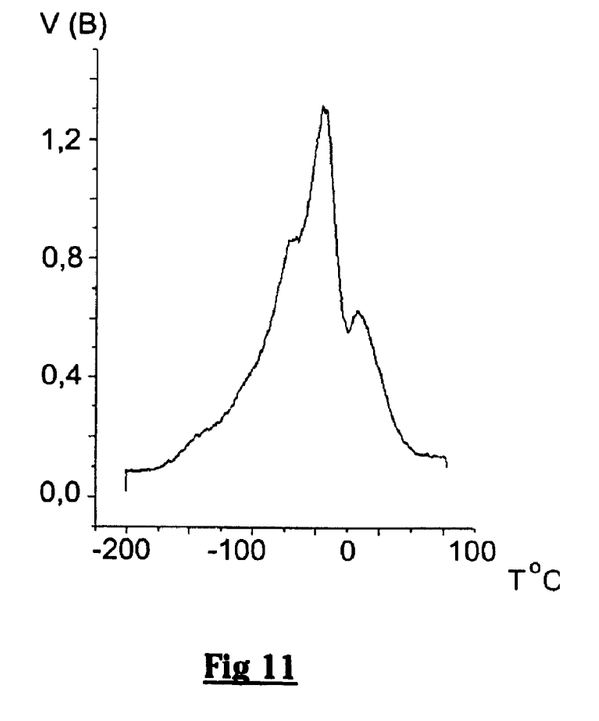
FIG. 11 shows a spectrum of the light emitted by a sample surface activated by an ion beam and then heated (example 3)
Figure 12:
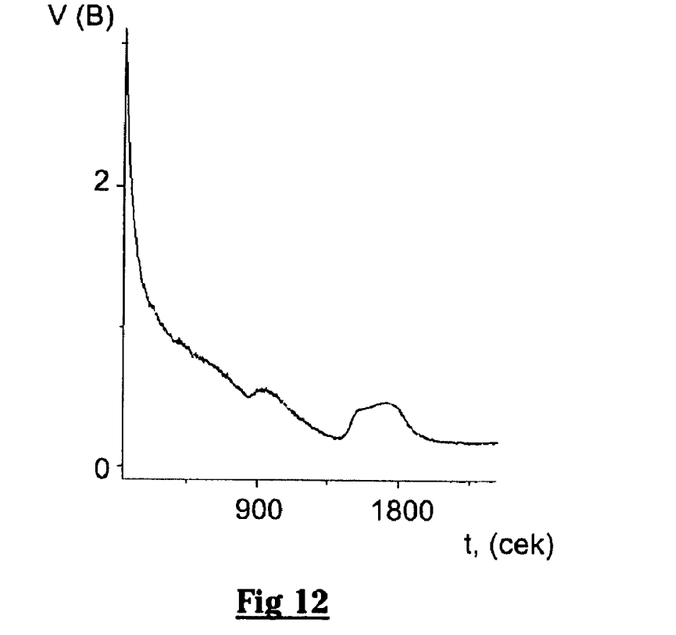
FIG. 12 shows a constant-temperature spectrum of the light emitted by a sample surface activated by a photon beam (example 3)
Figure 13:
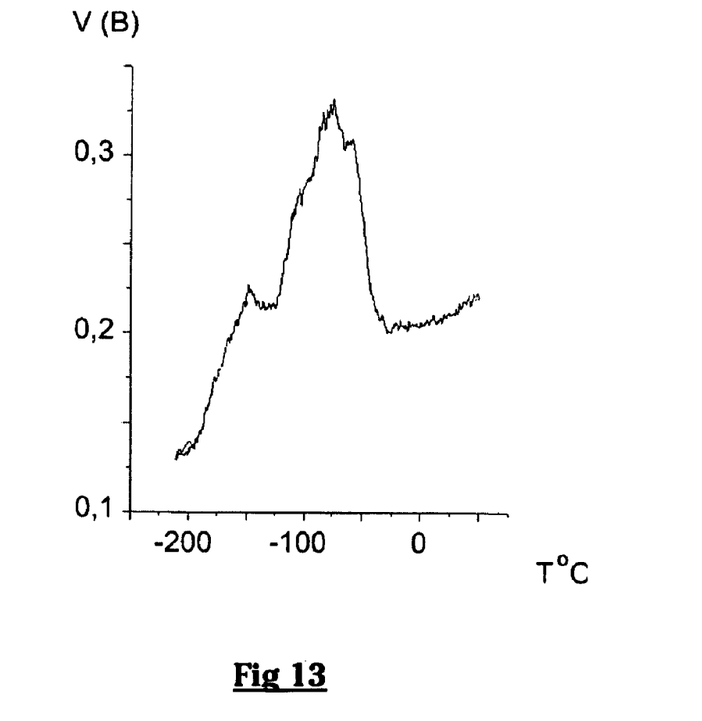
FIG. 13 shows a spectrum of the light emitted by a sample surface activated by a photon beam and then heated (example 3)

In example 2, a sample of quenched polyethylene of the same grade was irradiated under the same conditions as in example 1. The spectra of the light emitted by the surface layer are presented in FIG. 4 (at constant temperature) and in FIG. 5 (in the process of heating).

A comparison of the spectra of the light emitted by one and the same material, but prepared under different conditions, reveals a considerable difference in the properties of the surface layers of the material.

In example 3, a sample of quenched polyethylene of the same grade was irradiated. The surface layer of the sample was successively subjected to the action of unit pulses of the following beams: electron, molecular, ion, and photon; the spectra of the emitted light were consecutively recorded at a constant temperature and during heating (FIGS. 6 and 7, 8 and 9, 10 and 11, 12 and 13, respectively). The total irradiation power of the four abovementioned unit pulses per unit surface area of the sample was $10^{-3}$ W/cm$^2$. Each type of irradiation excites definite (specific for it) states in the surface layer of the sample; this makes it possible to characterize various physical and chemical properties of the surface layer more thoroughly and accurately (phase and relaxation transition temperatures, activation energies of these transitions, half-lives of loosely coupled surface states, chemical reactions occurring on the surface and their orders, etc.).

To infer information on the properties of the surface layer of a solid from the light radiation spectra, the known dependencies are used. For example, the most important parameter—the activation energy of relaxation transition (Ep)—can be found from the ratio $$Ep = \frac{RT_{max}^2}{T' - T_{max}}$$

where R is the gas constant,

T' is the temperature of the high-temperature wing of the thermoluminescence maximum at which the thermoluminescence is half the maximum intensity; and $T_{max}$ is the temperature at which maximum thermoluminescence is observed.

The order of the chemical reaction giving rise to isothermal luminescence is inferred from the dependence of the light emission intensity on time at a constant temperature in the coordinate system lnI-t, where I is the luminescence intensity and t is the time, or in the coordinate system I-1/t$^2$. If the dependence is linear in the former system, the chemical reaction is of the first order (decomposition). If the dependence is linear in the latter system, the chemical reaction is of the second order (recombination).

Figure 14:
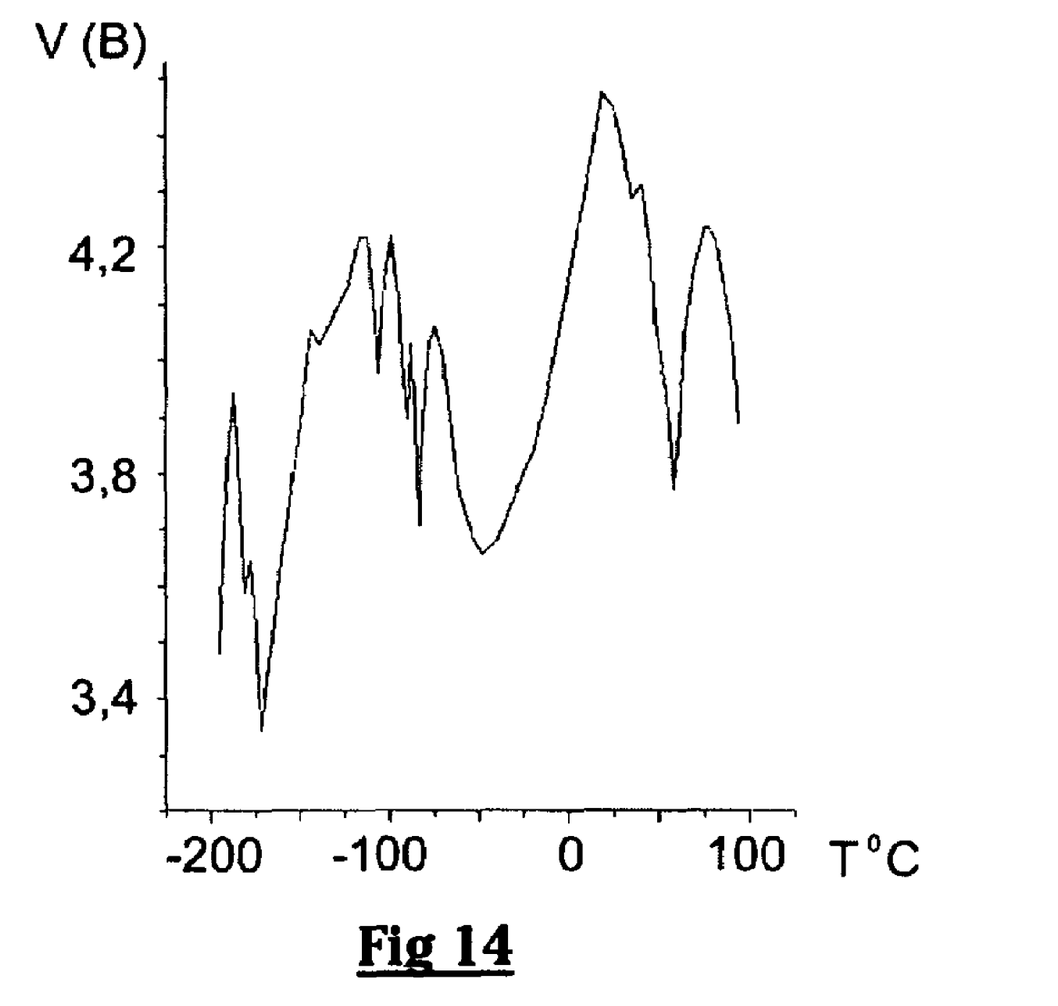
FIG. 14 shows a spectrum of the light emitted by a sample surface activated successively by an atom, electron, molecular, ion and photon beam and then heated (example 4)

In example 4, the overall effect of successive irradiation with unit pulses of atom, electron, molecular, ion, and photon beams on the surface layer of low-pressure polyethylene MOPLEN ($M_w$=114000) crystallized at the temperature close to the melting temperature was investigated. The total irradiation power per unit sample surface area was $5 \cdot 10^{-5}$ W\cm$^2$. A thermoluminescence spectrum was recorded when the material was heated (FIG. 14). The spectrum exhibits multiple peaks that give information on relaxation temperatures and energies of phase and relaxation transitions. It differs from the thermoluminescence spectra recorded when a similar sample was separately irradiated by unit pulses of abovementioned beams. Each type of irradiation excites definite (specific for it) states in the sample surface layer. The states previously excited by some irradiation react to another irradiation differently, which allows one to draw a conclusion on the behavior of the surface layer in the case of a combined irradiation which is frequently used in high technologies.

Figure 15:
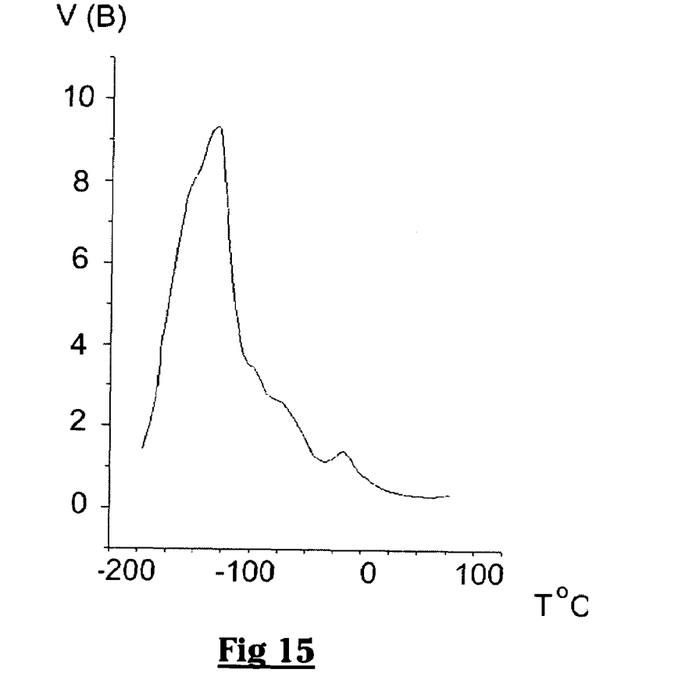
FIG. 15 shows a spectrum of the light emitted by a sample surface activated successively by an atom, electron, molecular, ion and photon beam and then heated (example 5)

In example 5, the overall effect of successive irradiation with unit pulses of electron, molecular, and ion beams on the surface layer of a sample of low-pressure polyethylene MOPLEN ($M_w$=114000) produced in the same way as in Example 4 was investigated. The total irradiation power per unit sample surface area was $3.7 \cdot 10^{-5}$ W\cm$^2$. A thermoluminescence spectrum was recorded when the material was heated (FIG. 15).

Figure 16:
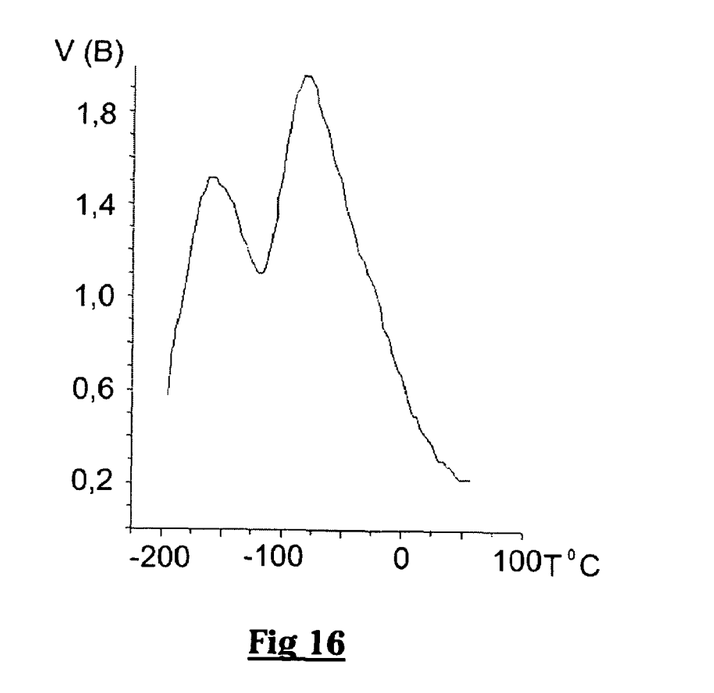
FIG. 16 shows a spectrum of the light emitted by a sample surface activated successively by an electron, photon, and ion beam and then heated (example 6)

In example 6, the overall effect of successive irradiation with unit pulses of electron, photon, and ion beams on the surface layer of a sample of low pressure polyethylene MOPLEN ($M_w$=114000) produced in the same way was investigated. The total irradiation power per unit sample surface area was $3.2 \cdot 10^{-5}$ W\cm$^2$. A thermoluminescence spectrum was recorded when the material was heated (FIG. 16).

In example 7, the overall effect of successive irradiation with unit pulses of atom and ion beams on the surface layer of a sample of low pressure polyethylene MOPLEN ($M_w$=114000) produced in the same way was investigated.

Figure 17:
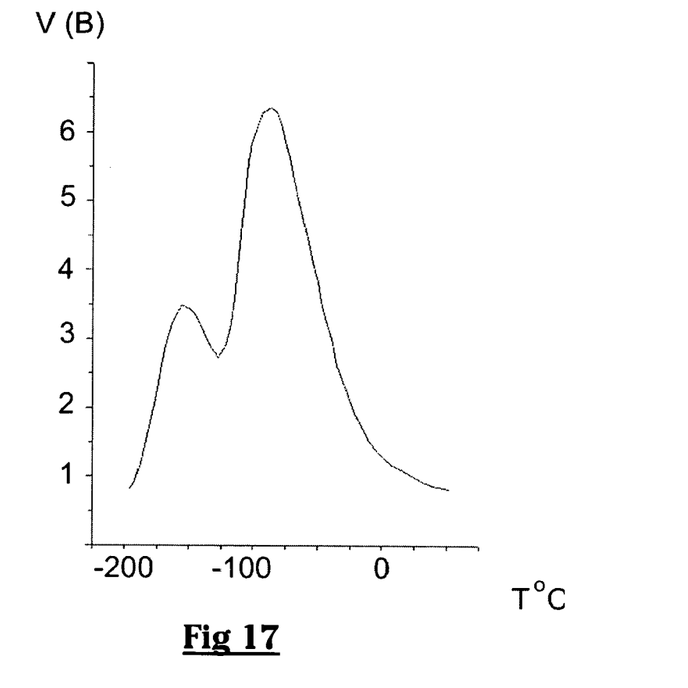
FIG. 17 shows a spectrum of the light emitted by a sample surface activated successively by an atom and ion beam and then heated (example 7)

The total irradiation power per unit sample surface area was 2.5·10$^{-5}$ W\cm$^2$. A thermoluminescence spectrum was recorded when the material was heated (FIG. 17).

A comparison of the thermoluminescence spectra recorded for the samples produced under the same conditions, but subjected to successive irradiation with unit pulses of electron, photon, molecular, atom and ion beams in different combinations, allows one to draw a conclusion about the nature of excitation of surface states in each example. Temperatures and energy characteristics of phase and relaxation transitions occurring at unfreezing of mobility of the excited surface are estimated from the positions of peaks.

The method as per claim 3 (second variant) is implemented as follows.

The sample 4 is fixed to the sample holder in the form of the container 3 and placed into the vacuum chamber 1; the air is evacuated from the vacuum chamber 1 through the main 14 down to a residual pressure of 1.33·10$^{-5}$ Pa. The pressure is controlled by the high-vacuum gauge 26. Then the trap 27 is filled with a coolant which results in adsorption of residual gases and water vapors on its surface. Subsequently, gas (hydrogen) is fed through the main 15 to the chamber 1 to a pressure of 13.3 Pa. The pressure in the chamber 1 is controlled by the low-vacuum gauge 13. The generator 9 equipped with the electrode 10 and also the electric discharge initiator 11 equipped with the electrode 12 are turned on. After the discharge is ignited in the chamber, the initiator 11 is turned off, and the generator 9 maintains the discharge in the plasma generating gas with a pressure from 4 to 8 Pa for a time period from 0.05 s to 5 s set by the timer. The spectrum of the energy (light) quanta emitted by the sample surface at a constant temperature is recorded. The monochromator 23 and the photomultiplier 24 are used to record the spectra; the output signal from the photomultiplier 24 comes to the data acquisition bus 18 and further, through the interface 17, to the computer 16. Then the sample 4 is heated by the heater 7, the sample temperature being controlled by the thermocouple 8. Signals from the thermocouple 8 and the photomultiplier 24 come to the data acquisition bus 18 and, through the interface 17, to the computer 16 for further processing.

Figure 18:
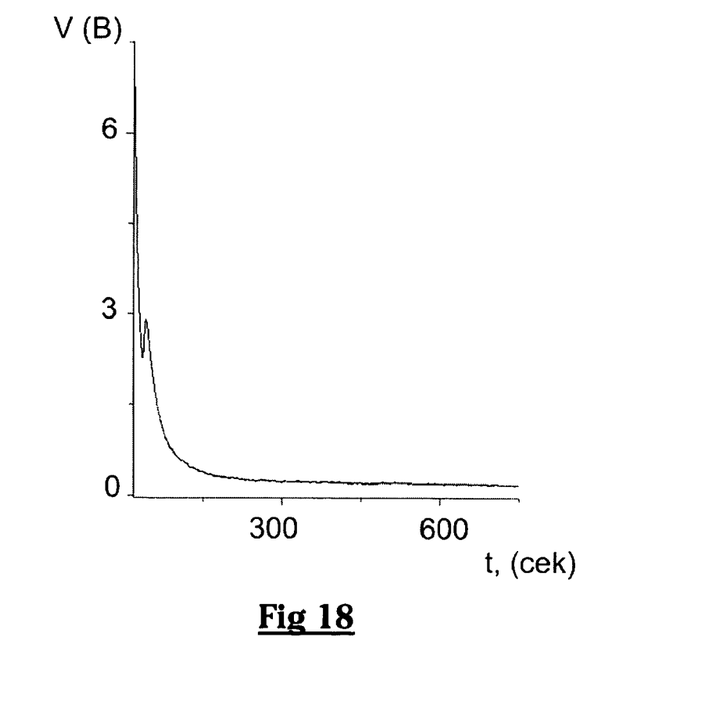
FIG. 18 shows a constant-temperature spectrum of the light emitted by a sample surface activated by LTP (example 8)
Figure 19:
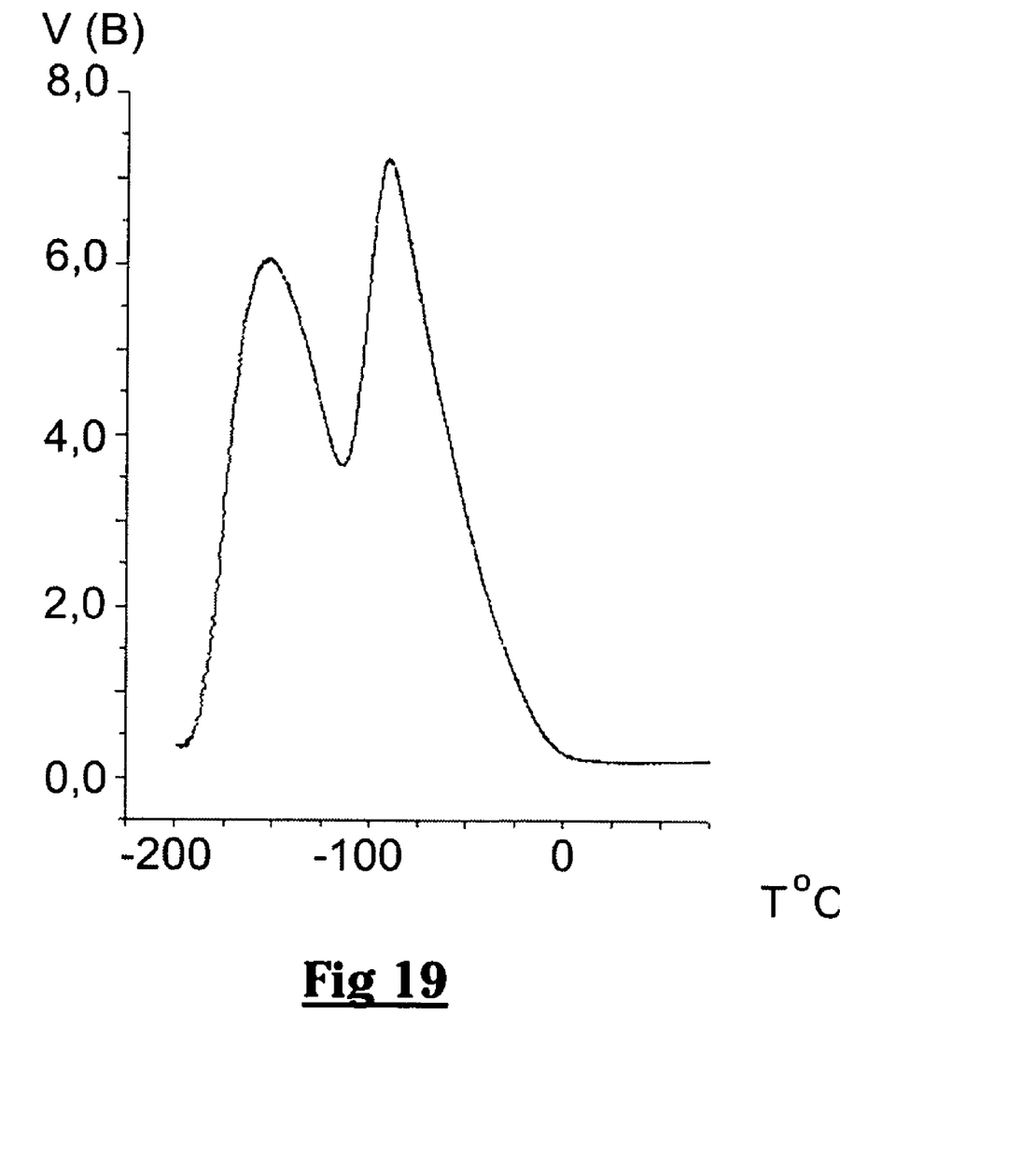
FIG. 19 shows a spectrum of the light emitted by a sample surface activated by LTP and then heated (example 8)
Figure 20:
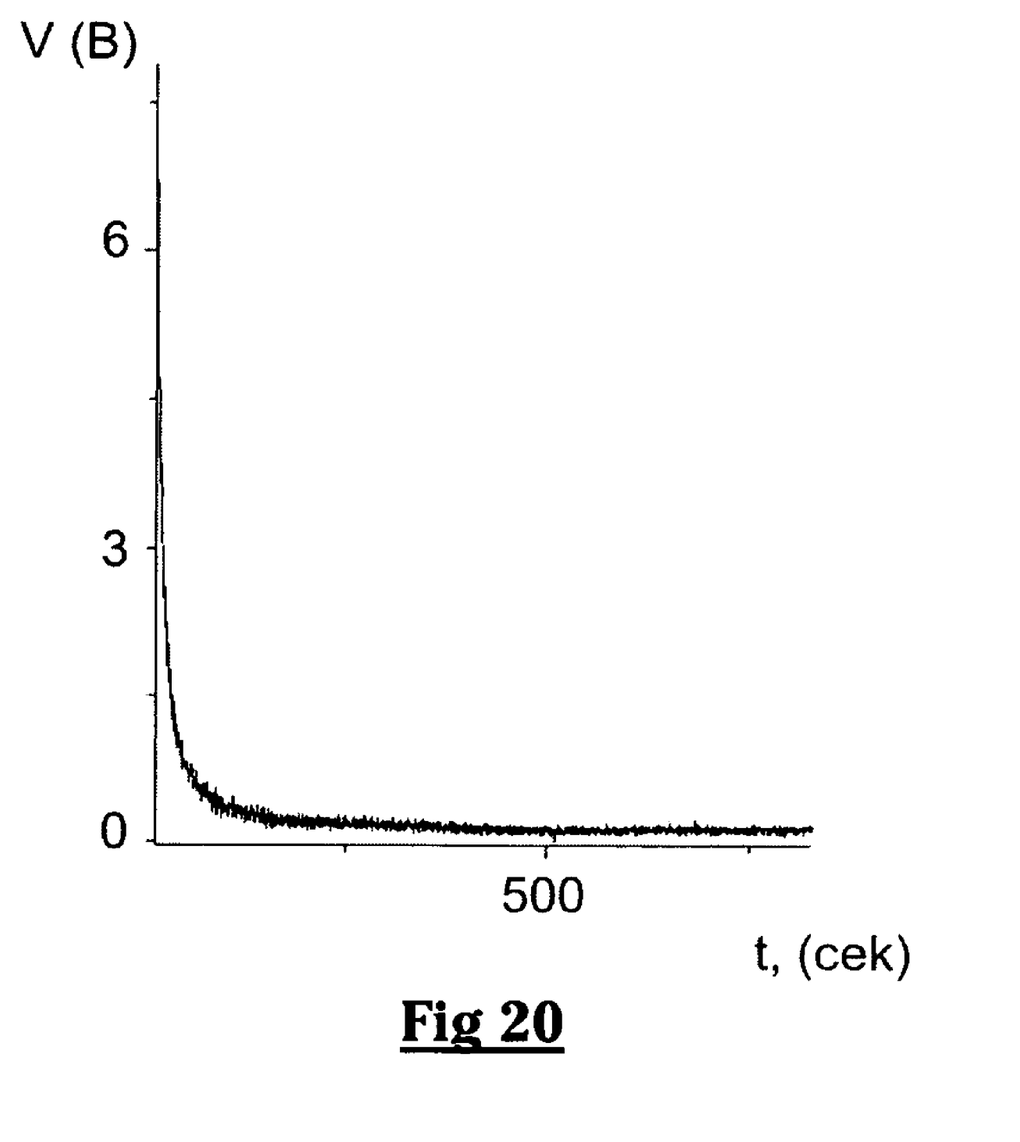
FIG. 20 shows a spectrum of the light emitted by a sample surface activated by LTP according to example 8 with the parameters described in the prototype.

In example 8, a surface layer of luminophor K11 was subjected to the action of LTP. The LTP with a plasma generating gas pressure of 4 Pa and a power of 2·10$^{-5}$ W/cm$^3$ for a period of 0.05 s was used. The light radiation spectra were recorded at a constant temperature of the sample (FIG. 18) and when it was heated (thermoluminescence) (FIG. 19). Methods of spectra processing were the same as in the abovementioned examples. A modifying influence of the irradiation (LTP) on the surface layer of the sample was found to be negligible. Due to the LTP parameters used, a pronounced feature in the spectrum of isothermal luminescence was observed, which was not revealed when the sample of the same material was subjected to the action of the LTP (in a reference experiment) with the parameters described in the prototype (FIG. 20).

Figure 21:
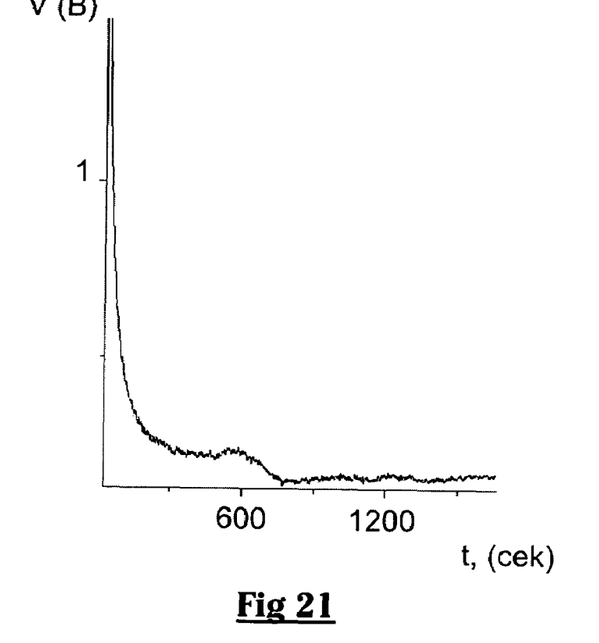
FIG. 21 shows a constant-temperature spectrum of the light emitted by a sample surface activated by LTP (example 9)
Figure 22:
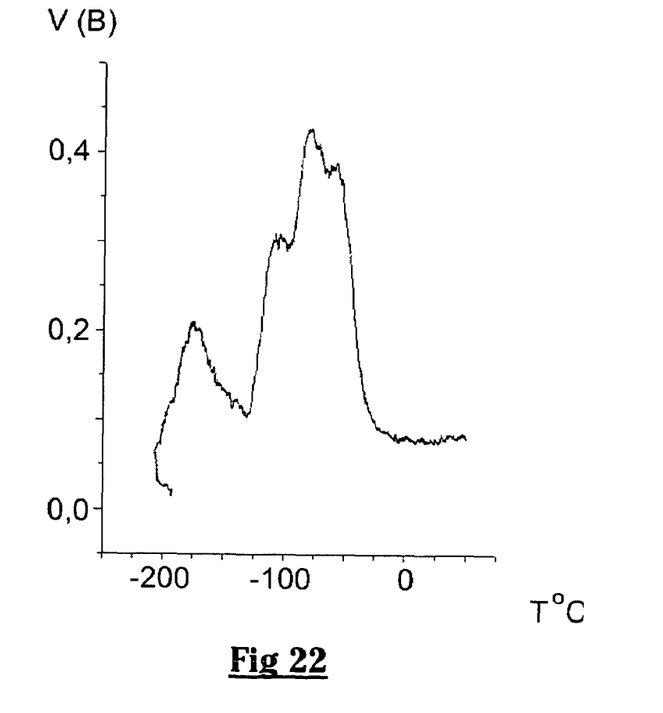
FIG. 22 shows a spectrum of the light emitted by a sample surface activated by LTP and then heated (example 9).

In example 9, the LTP with a plasma generating gas pressure of 6 Pa and a power of 7·10$^{-4}$ W/cm$^3$ for a period of 4.5 s was used. A sample of polyethylene MOPLEN ($M_w$=114000) crystallized at the temperature close to the melting temperature was irradiated. A constant-temperature light radiation spectrum is presented in FIG. 21, and the spectrum recorded during sample heating is shown in FIG. 22.

INDUSTRIAL APPLICABILITY

Commercially available constructive materials and equipment are used to fabricate the device for the implementation of the method (variants) of the present invention. In the applicant's opinion, the invention corresponds to the criterion "Industrial applicability" (IA).

The invention claimed is:
1. The method for analyzing physical and/or chemical properties of the surface layer of a solid comprising activation of said surface by low temperature plasma followed by deactivation of the surface layer and recording of the thermoluminescense spectrum, wherein the temperature plasma with a plasma generating gas pressure from 4 to 8 Pa for a period from 0.05 s to 5 s is used, radiation spectra are recorded at a constant temperature of the sample, and additional information on physical and chemical reactions in the surface layer of the solid is obtained from said radiation spectra showing the decreases in luminsescence from the moment the sample activation by the low-temperature plasma is over.

* * * * *

UNITED STATES PATENT AND TRADEMARK OFFICE
CERTIFICATE OF CORRECTION

PATENT NO. : 7,309,864 B2
APPLICATION NO. : 10/527966
DATED : December 18, 2007
INVENTOR(S) : Kalachev et al.

It is certified that error appears in the above-identified patent and that said Letters Patent is hereby corrected as shown below:

Title page, Item (75) Inventors should include
-- Lyubov Petrovna Myasnikova, Sankt-Peterburg, RU --.

Fifth Inventor name should read
-- Alexandr Lvovich Myasikov --.

Signed and Sealed this

Second Day of September, 2008

JON W. DUDAS
*Director of the United States Patent and Trademark Office*